(12) United States Patent
Feinberg et al.

(10) Patent No.: US 11,491,005 B2
(45) Date of Patent: Nov. 8, 2022

(54) ADJUSTABLE IMPLANT

(71) Applicant: MENTOR WORLDWIDE LLC, Irvine, CA (US)

(72) Inventors: Marc Feinberg, Ringoes, NJ (US); Michael Hoffman, Somerset, NJ (US)

(73) Assignee: MENTOR WORLDWIDE LLC, Irvine, CA (US)

( * ) Notice: Subject to any disclaimer, the term of this patent is extended or adjusted under 35 U.S.C. 154(b) by 333 days.

(21) Appl. No.: 17/001,307

(22) Filed: Aug. 24, 2020

(65) Prior Publication Data
US 2020/0383773 A1 Dec. 10, 2020

Related U.S. Application Data

(62) Division of application No. 15/693,965, filed on Sep. 1, 2017, now Pat. No. 10,751,163.

(51) Int. Cl.
*A61F 2/12* (2006.01)
*A61B 90/00* (2016.01)
(Continued)

(52) U.S. Cl.
CPC ............ *A61F 2/12* (2013.01); *A61B 90/02* (2016.02); *F04B 43/028* (2013.01); *A61F 2/484* (2021.08);
(Continued)

(58) Field of Classification Search
CPC .... A61F 2/12; A61F 2/484; A61F 2210/0057; A61F 2230/0065; A61F 2250/0003;
(Continued)

(56) References Cited

U.S. PATENT DOCUMENTS

| 146,805 A | 1/1874 | Cox |
| 1,091,063 A | 3/1914 | Hutchinson |

(Continued)

FOREIGN PATENT DOCUMENTS

| DE | 19923183 A1 | 11/2000 |
| EP | 1 547 549 A2 | 6/2005 |

(Continued)

OTHER PUBLICATIONS

Extended European Search Report for European Application No. 17158382.6-1664, dated Jul. 27, 2017, 8 pages.

(Continued)

*Primary Examiner* — Suzette J Gherbi
(74) *Attorney, Agent, or Firm* — Etan S. Chatlynne; Calderon Safran & Cole, P.C.

(57) ABSTRACT

The present disclosure describes various embodiments of adjustable implants, particularly permanent breast implants, intended for implantation into a subject, particularly a human subject. In some embodiments, the adjustable implant comprises a shell including a resilient shell membrane, a first reservoir containing a fluid, e.g., a saline, a second reservoir including a resilient second-reservoir membrane, and a pump. The pump may include a first pump actuator, a first pump inlet, and a first pump outlet. The first reservoir and second reservoir may be disposed within the shell and be in fluid communication via the pump. Fluid may be transferred between the two reservoirs to change the profile of the implant.

7 Claims, 10 Drawing Sheets

(51) Int. Cl.
*F04B 43/02* (2006.01)
*A61F 2/48* (2006.01)

(52) U.S. Cl.
CPC .............. *A61F 2210/0057* (2013.01); *A61F 2230/0065* (2013.01); *A61F 2250/0003* (2013.01); *A61F 2250/0004* (2013.01); *A61F 2250/0013* (2013.01)

(58) Field of Classification Search
CPC ..... A61F 2250/0004; A61F 2250/0013; A61B 90/02; F04B 43/028
USPC ........................................................ 623/12
See application file for complete search history.

(56) References Cited

U.S. PATENT DOCUMENTS

| | | | |
|---|---|---|---|
| 1,263,798 | A | 4/1918 | Otto |
| 3,852,833 | A | 12/1974 | Koneke et al. |
| 3,919,724 | A | 11/1975 | Sanders et al. |
| 3,934,274 | A | 1/1976 | Hartley, Jr. |
| 4,433,440 | A | 2/1984 | Cohen |
| 4,615,704 | A | 10/1986 | Frisch |
| 4,624,671 | A | 11/1986 | Kress |
| 4,643,733 | A | 2/1987 | Becker |
| 4,773,908 | A | 9/1988 | Becker |
| 4,775,379 | A | 10/1988 | Fogarty et al. |
| 4,790,309 | A | 12/1988 | Becker |
| 4,944,749 | A | 7/1990 | Becker |
| 4,969,892 | A | 11/1990 | Burton et al. |
| 4,969,898 | A | 11/1990 | Calogero |
| 4,969,899 | A | 11/1990 | Cox |
| 5,019,101 | A | 5/1991 | Purkait et al. |
| 5,181,907 | A | 1/1993 | Becker |
| 5,219,360 | A | 6/1993 | Georgiade |
| 5,507,808 | A | 4/1996 | Becker |
| 5,549,672 | A | 8/1996 | Maddock et al. |
| 5,630,843 | A | 5/1997 | Rosenberg |
| 5,723,006 | A * | 3/1998 | Ledergerber ............ A61F 2/12 600/233 |
| 5,776,159 | A | 7/1998 | Young |
| 5,845,813 | A | 12/1998 | Werner |
| 5,882,353 | A | 3/1999 | VanBeek et al. |
| 6,113,569 | A | 9/2000 | Becker |
| 6,183,514 | B1 | 2/2001 | Becker |
| 6,540,702 | B1 | 4/2003 | Sarango |
| 6,755,861 | B2 | 6/2004 | Nakao |
| 7,081,136 | B1 | 7/2006 | Becker |
| 7,615,074 | B2 | 11/2009 | Carvalio |
| 7,762,982 | B1 | 7/2010 | Shah |
| 3,080,057 | A1 | 12/2011 | Kronowitz |
| 8,197,542 | B2 | 6/2012 | Becker |
| 8,202,317 | B2 | 6/2012 | Becker |
| 8,308,630 | B2 | 11/2012 | Birk et al. |
| 8,394,118 | B2 | 3/2013 | Jones et al. |
| 8,398,710 | B2 | 3/2013 | Forsell |
| 9,265,921 | B2 | 2/2016 | Korman |
| 10,548,712 | B2 | 2/2020 | Govari et al. |
| 2002/0011497 | A1 | 1/2002 | Farris |
| 2005/0284215 | A1 | 12/2005 | Falsetti |
| 2006/0069403 | A1 | 3/2006 | Shalon et al. |
| 2006/0100578 | A1 | 5/2006 | Liberman |
| 2006/0161196 | A1 | 7/2006 | Widgerow |
| 2007/0050026 | A1 | 3/2007 | Carvalio |
| 2007/0276478 | A1 | 11/2007 | Marmureanu et al. |
| 2008/0275569 | A1 | 11/2008 | Lesh |
| 2009/0210056 | A1 | 8/2009 | Forsell |
| 2010/0010531 | A1 | 1/2010 | Shalon et al. |
| 2010/0010871 | A1 | 1/2010 | Mengerink |
| 2010/0087843 | A1 | 4/2010 | Bertolote et al. |
| 2010/0108717 | A1 | 5/2010 | Szymanski |
| 2010/0204792 | A1 | 8/2010 | Greco |
| 2010/0211166 | A1 | 8/2010 | Miller et al. |
| 2010/0228347 | A1 | 9/2010 | Schuessler |
| 2010/0324688 | A1 | 12/2010 | Doty |
| 2011/0106249 | A1 | 5/2011 | Becker |
| 2011/0153017 | A1 | 6/2011 | McClellan |
| 2011/0160854 | A1 | 6/2011 | Berg et al. |
| 2011/0160859 | A1 | 6/2011 | Doty |
| 2011/0230845 | A1 | 9/2011 | Pascal et al. |
| 2011/0264213 | A1 | 10/2011 | DeMiranda |
| 2012/0059349 | A1 | 3/2012 | Kuo et al. |
| 2012/0116509 | A1 | 5/2012 | Forsell |
| 2013/0007980 | A1 | 1/2013 | Worker et al. |
| 2013/0013063 | A1 | 1/2013 | DelVecchio |
| 2013/0013084 | A1 * | 1/2013 | Birk ............... A61F 5/0076 606/191 |
| 2013/0079807 | A1 | 3/2013 | Korman |
| 2013/0237915 | A1 | 9/2013 | Barrelli |
| 2013/0245758 | A1 | 9/2013 | Chitre et al. |
| 2013/0341353 | A1 | 12/2013 | Harris |
| 2014/0031619 | A1 | 1/2014 | Moon |
| 2014/0100656 | A1 | 4/2014 | Namnoum et al. |
| 2014/0142556 | A1 | 5/2014 | Kuo et al. |
| 2014/0156001 | A1 | 6/2014 | Davodian |
| 2014/0200396 | A1 | 7/2014 | Lashinski et al. |
| 2014/0221732 | A1 | 8/2014 | Dayton et al. |
| 2014/0222145 | A1 | 8/2014 | Kronowitz |
| 2014/0236210 | A1 * | 8/2014 | Payne ................. A61F 2/12 606/192 |
| 2015/0038976 | A1 | 2/2015 | Roschak et al. |
| 2015/0374906 | A1 | 12/2015 | Forsell |
| 2016/0045312 | A1 | 2/2016 | Braido et al. |
| 2016/0228603 | A1 | 8/2016 | Nguyen et al. |
| 2016/0250017 | A1 | 9/2016 | McClellan |
| 2016/0310711 | A1 | 10/2016 | Luxon et al. |
| 2017/0079737 | A1 * | 3/2017 | Jones ................ A61M 29/02 |
| 2017/0127929 | A1 * | 5/2017 | Schutt ............... A61B 17/7065 |
| 2017/0165025 | A1 * | 6/2017 | Payne ................ A61B 90/02 |
| 2017/0333179 | A1 * | 11/2017 | Forsell .................. A61F 2/12 |
| 2018/0153684 | A1 | 6/2018 | Van Heugten et al. |
| 2018/0200714 | A1 | 7/2018 | Viovy et al. |
| 2018/0279889 | A1 | 10/2018 | Lee |
| 2019/0091001 | A1 | 3/2019 | Forsell |
| 2019/0111206 | A1 * | 4/2019 | Forsell .................. F04C 2/10 |
| 2019/0223971 | A1 * | 7/2019 | Payne .................. A61F 2/12 |

FOREIGN PATENT DOCUMENTS

| | | |
|---|---|---|
| EP | 2 453 839 B1 | 3/2014 |
| WO | 95/04561 A1 | 2/1995 |
| WO | 2016/003718 A1 | 1/2016 |

OTHER PUBLICATIONS

International Search Report and Written Opinion for International Application No. PCT/IB2018/056354, dated Nov. 16, 2018, 12 pages.

"Becker Expander/Mammary Prostheses (Reconstruction Adjunct Study)", Mentor, 2002 http://www.mentorwwlic.com/Documents/Becker.pdf.

* cited by examiner

ADJUSTABLE IMPLANT

CROSS-REFERENCE TO CO-PENDING APPLICATION

The present application is a Divisional Application under 35 U.S.C. § 121 of U.S. patent application Ser. No. 15/693,965, filed Sep. 1, 2017. The entire content of this application is incorporated by reference herein in its entirety.

FIELD

The subject matter disclosed herein relates to breast implants for use in a subject.

BACKGROUND

Tissue expanders are used to assist in stretching skin of a subject to provide a tissue pocket or capsule having an appropriate size to accommodate a permanent implant, such as a breast implant. In typical usage, the tissue expander is implanted into a subject to help prepare the subject to receive a permanent breast implant. The tissue expander may be expanded by introducing additional material therein, e.g., saline, until the desired size of the pocket or capsule is achieved, at which point the tissue expander may be removed. A permanent breast implant may then be implanted into the subject.

Certain tissue expanders may be used as an adjustable breast implant, such as the Becker Expander/Mammary Prostheses manufactured by Mentor of Irvine, Tex. This adjustable implant utilizes a fill tube through which saline may be introduced or removed from the implant to change the implant's size. Thus, the adjustable implant may be used to change the size of the capsule. Once the desired size of the capsule is achieved, the fill tube may be removed from the implant, thereby rendering the implant non-adjustable. The implant may remain in the capsule.

SUMMARY

The present disclosure describes various embodiments of adjustable implants, particularly permanent breast implants, intended for implantation into a subject, particularly a human subject. In some embodiments, the adjustable implant comprises a shell including a resilient shell membrane, a first reservoir containing a fluid, e.g., a saline, a second reservoir including a resilient second-reservoir membrane, and a pump. The pump may include a first pump actuator, a first pump inlet, and a first pump outlet. The first reservoir and second reservoir may be disposed within the shell and be in fluid communication via the pump.

In some embodiments, the adjustable implant may also include a first tube connected to the first reservoir and the first pump inlet, and a second tube connected to the first pump outlet and the second reservoir. A first valve may be disposed proximate the first pump outlet. The first valve may be a backflow prevention valve having a first-valve outlet disposed further from the first pump actuator than a first-valve inlet.

In some embodiments, the pump may additionally include a second pump actuator. In other embodiments, the pump may alternatively or additionally include a release actuator. The release actuator may be disposed proximate the first valve.

In some embodiments, the pump may be disposed proximate the shell membrane such that a portion of the pump is disposed within the resilient shell membrane and the first pump actuator is disposed upon the resilient shell membrane. In other embodiments, the pump is disposed within the shell membrane.

In some embodiments, the pump includes a second valve disposed proximate the first pump inlet. The second valve may be a backflow prevention valve having a second-valve inlet disposed further from the first pump actuator than a second-valve outlet. In these embodiments, the release actuator may include a first arm disposed adjacent to the first-valve outlet a second arm disposed adjacent to the second-valve outlet.

In some embodiments, the first pump actuator comprises an elastomeric button that defines a chamber disposed between the first pump inlet and the first pump outlet.

In some embodiments, the first reservoir has a toroidal configuration, whereas in other embodiments the first reservoir has a domed configuration.

Various embodiments of the adjustable implant disclosed herein may be used according to the following exemplary methods. An adjustable implant may be provided. For example, the adjustable implant may be of the embodiments having a shell including a resilient shell membrane, a first reservoir disposed within the shell and containing a first volume of a fluid; e.g., a saline, a second reservoir including a resilient elastomeric second-reservoir membrane disposed within the shell, a pump having a pump outlet, a pump actuator comprising an elastomeric button that defines a chamber containing a second volume of the fluid, and a first valve disposed proximate the pump outlet, the first reservoir and second reservoir being in fluid communication via the pump and the first valve. The elastomeric button may be depressed. At least a portion of the second volume of fluid may be advanced past the first valve. The elastomeric button may be released. A third volume of fluid may be withdrawn from the first reservoir.

The method may also include the steps of introducing a fourth volume of the fluid into the second reservoir, expanding the resilient elastomeric second-reservoir membrane to account for the fourth volume of the fluid entering the second reservoir, and expanding the resilient shell membrane in response to expanding the resilient elastomeric second-reservoir membrane.

For those embodiments where the pump also includes a release actuator disposed proximate the first valve and configured to open the first valve when actuated, the method may also include the steps of actuating the release actuator, opening the first valve to allow a fifth volume of the fluid to exit the second reservoir and flow toward the first reservoir, contracting the resilient elastomeric second-reservoir membrane to account for the fifth volume of fluid exiting the second reservoir, and contracting the resilient shell membrane in response to contracting the resilient elastomeric second-reservoir membrane.

In those embodiments in which the pump includes a pump inlet, the adjustable implant includes a second valve disposed proximate the pump inlet, and the release actuator is disposed proximate the second valve and configured to open the second valve when actuated, the method may also include the step of opening the second valve using the release actuator.

In those embodiments where the adjustable implant is a breast implant, the method may further include implanting the breast implant into a subject, particularly a human subject.

BRIEF DESCRIPTION OF THE DRAWINGS

While the specification concludes with claims which particularly point out and distinctly claim the subject matter described herein, it is believed the subject matter will be better understood from the following description of certain examples taken in conjunction with the accompanying drawings, in which like reference numerals identify the same elements and in which:

FIG. 4 further details features and components of the adjustable implant of

FIG. 1;

DETAILED DESCRIPTION

The following description sets forth certain illustrative examples of the claimed subject matter. Other examples, features, aspects, embodiments, and advantages of the technology should become apparent to those skilled in the art from the following description. Accordingly, the drawings and descriptions should be regarded as illustrative in nature.

Figure 1:
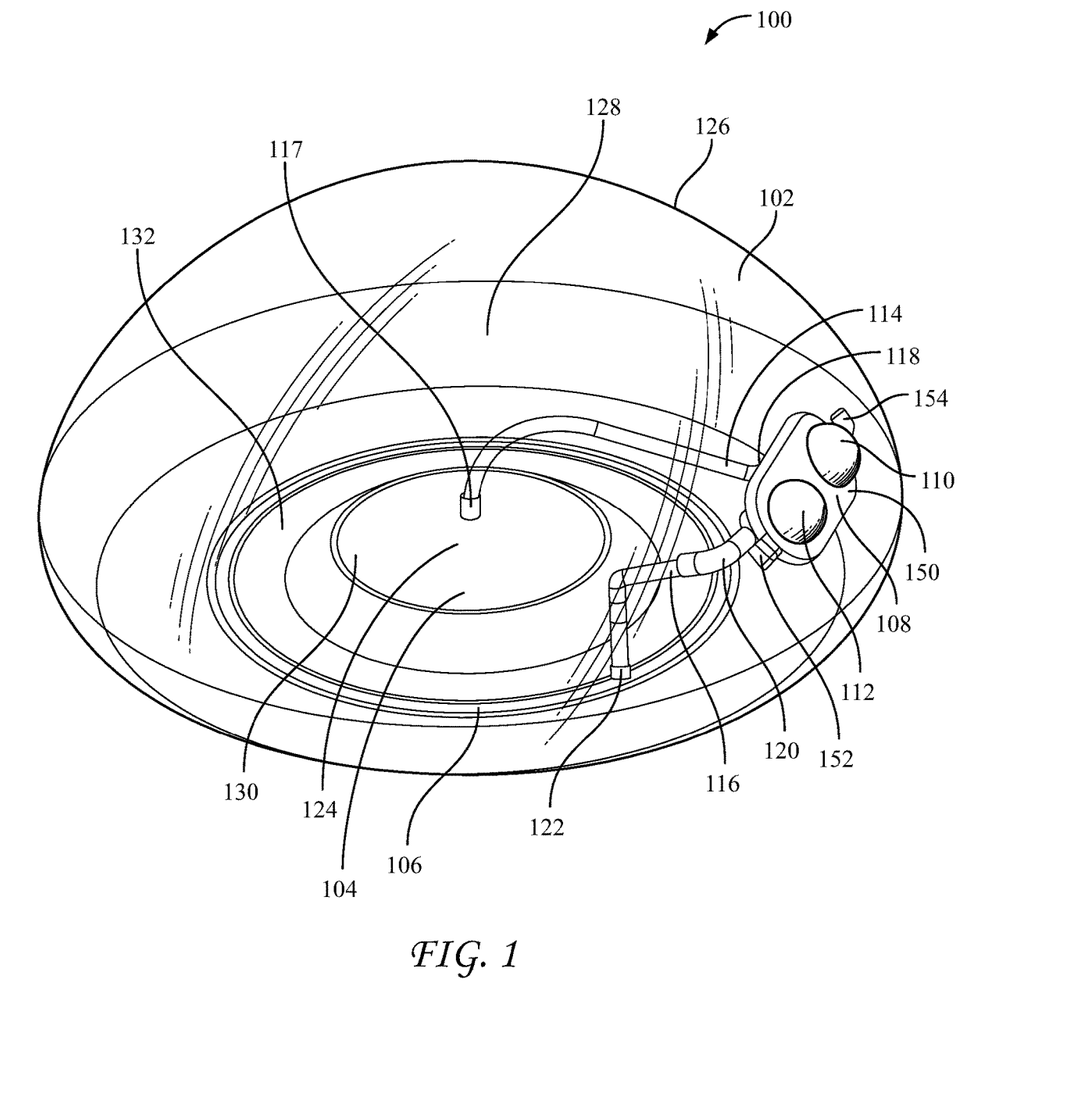
FIG. 1 depicts an adjustable implant in a rest state.
Figure 2:
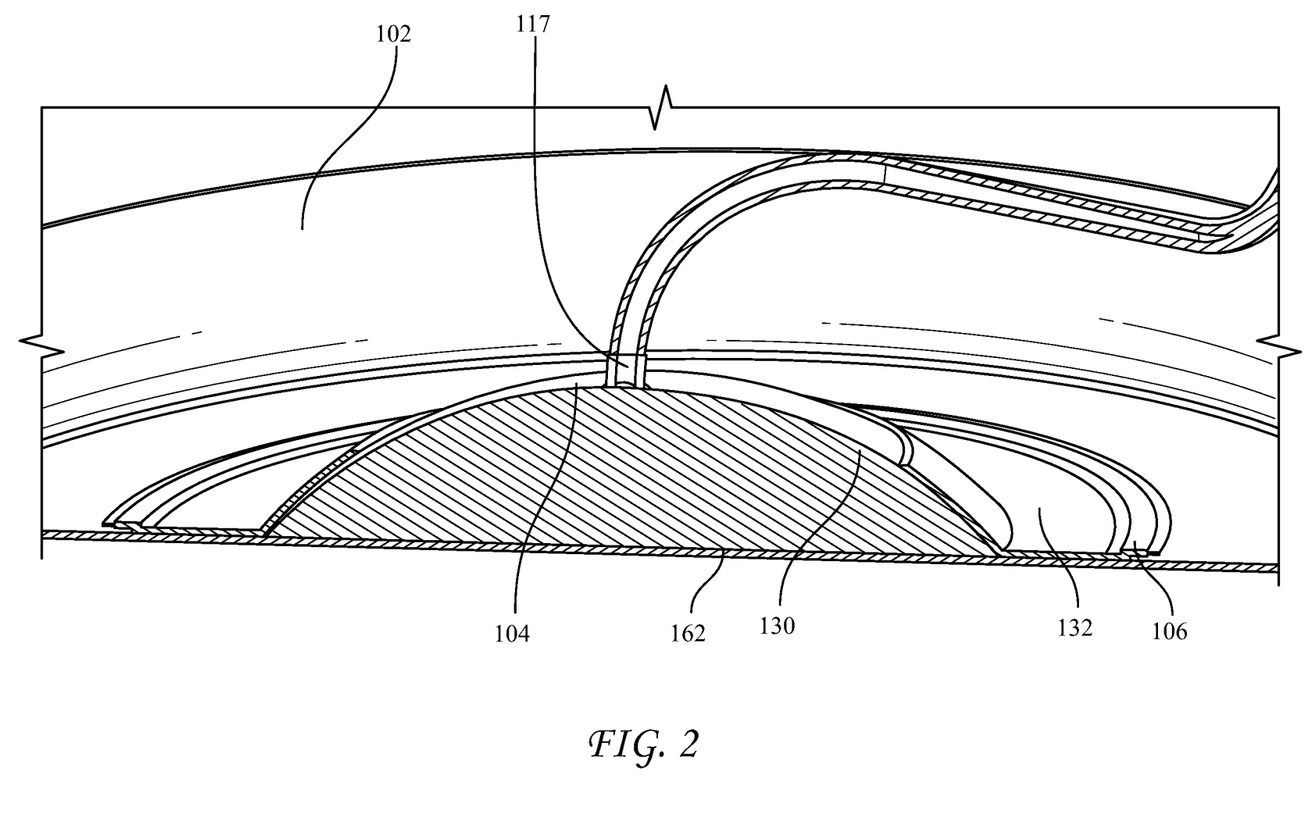
FIG. 2 depicts a magnified cross-sectional view of a portion of the adjustable implant of FIG. 1.

FIG. 1 is a representation of an exemplary embodiment of the present subject matter, i.e., adjustable implant 100. Adjustable implant 100 includes a shell 102 that contains a first reservoir 104, a second reservoir 106, and a pump 108. Pump 108 may include a pump actuator 110 and a release actuator 112. First reservoir 104 and second reservoir 106 are fluidly connected by tube 114, pump 108, and tube 116. Tube 114 is connected to a port 117 of first reservoir 104 and an inlet 118 of pump 108. Tube 116 is connected to an outlet 120 of pump 108 and a port 122 of second reservoir 106. A fluid 124, e.g., a gas, such as air, or a liquid, such as saline, may be contained within at least one of first reservoir 104 and second reservoir 106. As shown in FIGS. 1 and 2, first reservoir 104 contains some or all of fluid 124 (some fluid may also be in pump 108 and tubes 114 and 116) and second reservoir 106 may be mostly or entirely empty.

Shell 102 includes a shell membrane 126 that may be fabricated from any resilient and/or stretchable material used to fabricate conventional implants, particularly breast implants. For example, elastomeric silicones, such as silicone rubber, may be used to fabricate shell membrane 126. Shell 102 may be filled with a material 128 to maintain a desired form and prevent shell membrane 126 from collapsing and deforming under its own weight. In some embodiments, shell 102 has the form of a conventional breast implant, which is the form of shell 102 reflected in the figures. Further, material 128 may provide compliance and/or resiliency when shell membrane is subject to external forces generated by, e.g., foreign objects or a subject's anatomy. The material 128 may be, e.g., an elastomer, such as silicone rubber, a silicone gel, or a liquid, such as saline. Notably, adjustable implant 100 is entirely self-contained, like a conventional permanent implant, but unlike conventional tissue expanders or the Becker Expander/Mammary Prostheses. That is no fluids, liquids, or other materials are introduced or removed from within the boundary defined by shell membrane 126.

First reservoir 104 may be defined by a rigid enclosure 130, which may be dome shaped, capable of resisting deformation such that the volume of enclosure 130 does not change as a function of the amount of fluid reservoir 104 contains or in response to external forces upon shell 102 or upon enclosure 130. Enclosure 130 may be, e.g., a metal material, such as stainless steel, a polymeric material, such as polycarbonate. In certain embodiments, it may be desirable for enclosure 130 to be semi-rigid, such that it is capable of deforming slightly in response to outside forces or as a function of the amount of fluid contained therein. In these embodiments, enclosure 130 may be a resilient yet stiff, thick, or high-durometer silicone rubber. In some embodiments, first reservoir 104 is disposed on an inner surface of shell membrane 126. First reservoir 104 may be attached or affixed to the inner surface of shell membrane 126 by any suitable means, including, for example, ultrasonic welding or silicone glue. In some embodiments, a base 162 of first reservoir 104 may be flexible to help prevent back-pressure from being generated within reservoir 104 that may resist withdrawal of fluid therefrom.

Second reservoir 106 may be defined by a resilient elastomeric second-reservoir membrane 132. Membrane 132 is fabricated from a resilient and expandable material, such as an elastomeric silicone or silicone rubber. Accordingly, membrane 132 may stretch and/or expand in response to a material, such as fluid 124, being introduced into second reservoir 106. As shown in FIGS. 1 and 2, second reservoir 106 is disposed on an inner surface of shell 102 and is empty of fluid. Thus second reservoir 106 is in a rest state (i.e., unexpanded and unstretched) such that membrane 132 is disposed flush against a bottom surface of reservoir 106 or directly against the inner surface of shell 102. Second reservoir 106 may be attached or affixed to an inner surface of shell membrane 126 by any suitable means, including, for example, ultrasonic welding or silicone glue. As shown in the figures, second reservoir 106 is disposed concentrically around first reservoir 104. Further, in addition to being attached or affixed to the inner surface of shell membrane 126, second reservoir 106 is also attached or affixed to enclosure 130 by any suitable means, including, for example, ultrasonic welding or silicone glue.

Figure 6:
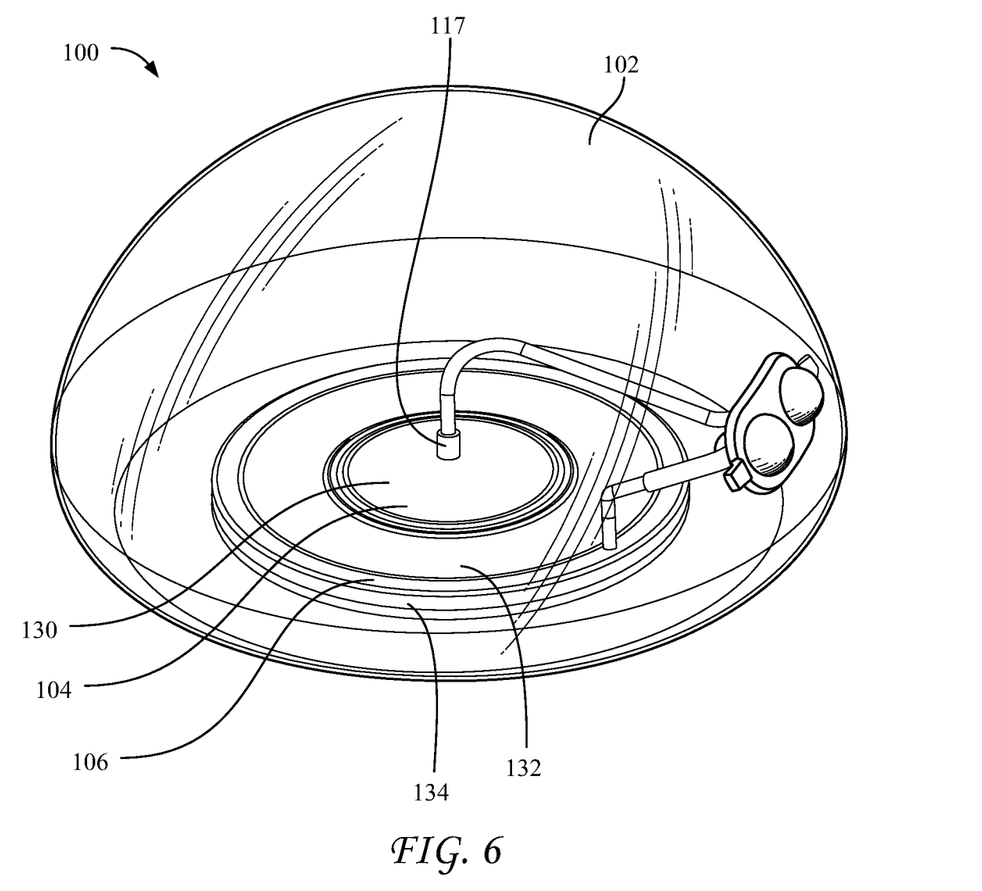
FIG. 6 depicts the adjustable implant of FIG. 1 in an expanded state.
Figure 7:
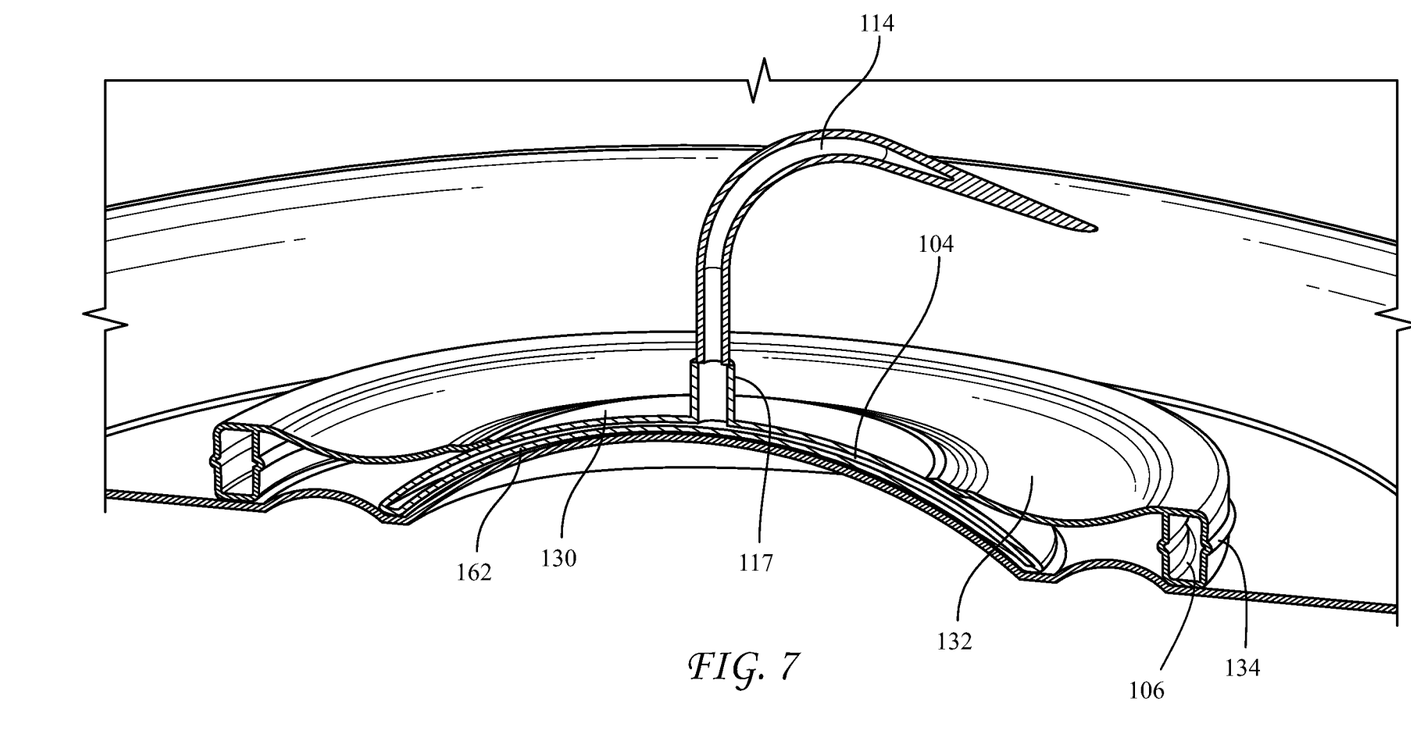
FIG. 7 depicts a magnified cross-sectional view of a portion of the adjustable implant of FIG. 1 in the expanded state of FIG. 6.

In certain embodiments, second reservoir 106 is structured or configured to expand by modes instead of or in addition to stretching. For example, as shown in FIGS. 6 and 7, second reservoir 106 may include bellows features, such as pleats 134. Pleats 134 may unfold in response to pressures generated from within second reservoir 106, i.e., by the introduction of fluid 124 therein. Thus second-reservoir membrane 132 may expand by a combination of stretching and unfolding as fluid 124 is pumped from first reservoir 104 into second reservoir 106. So expanded, membrane 132 no longer rests flush against its base or an inner surface of shell 102. Instead, membrane 132 is displaced therefrom by the fluid pumped into second reservoir 106.

Figure 3:
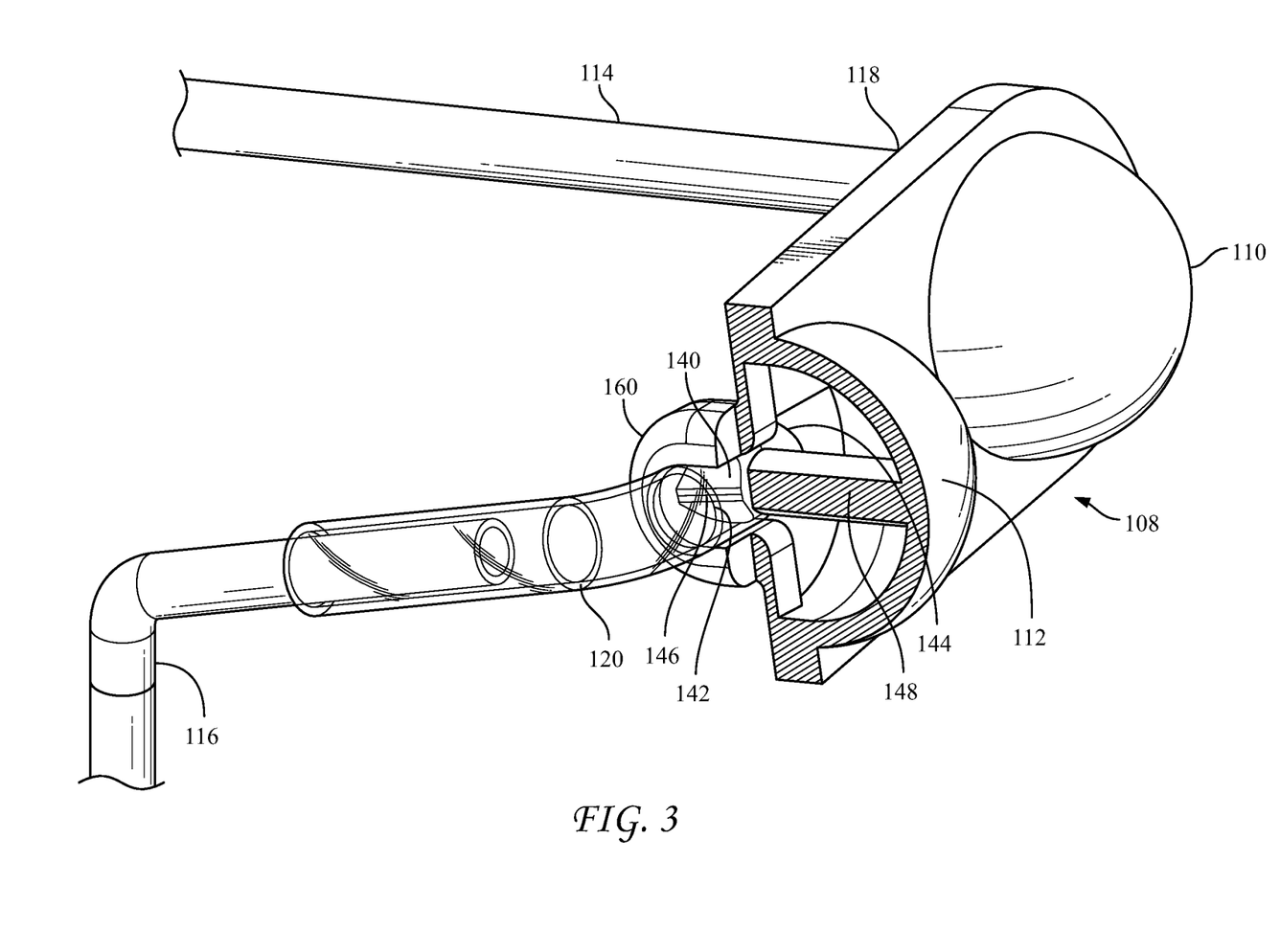
FIG. 3 details features and components of the adjustable implant of FIG. 1.
Figure 4:
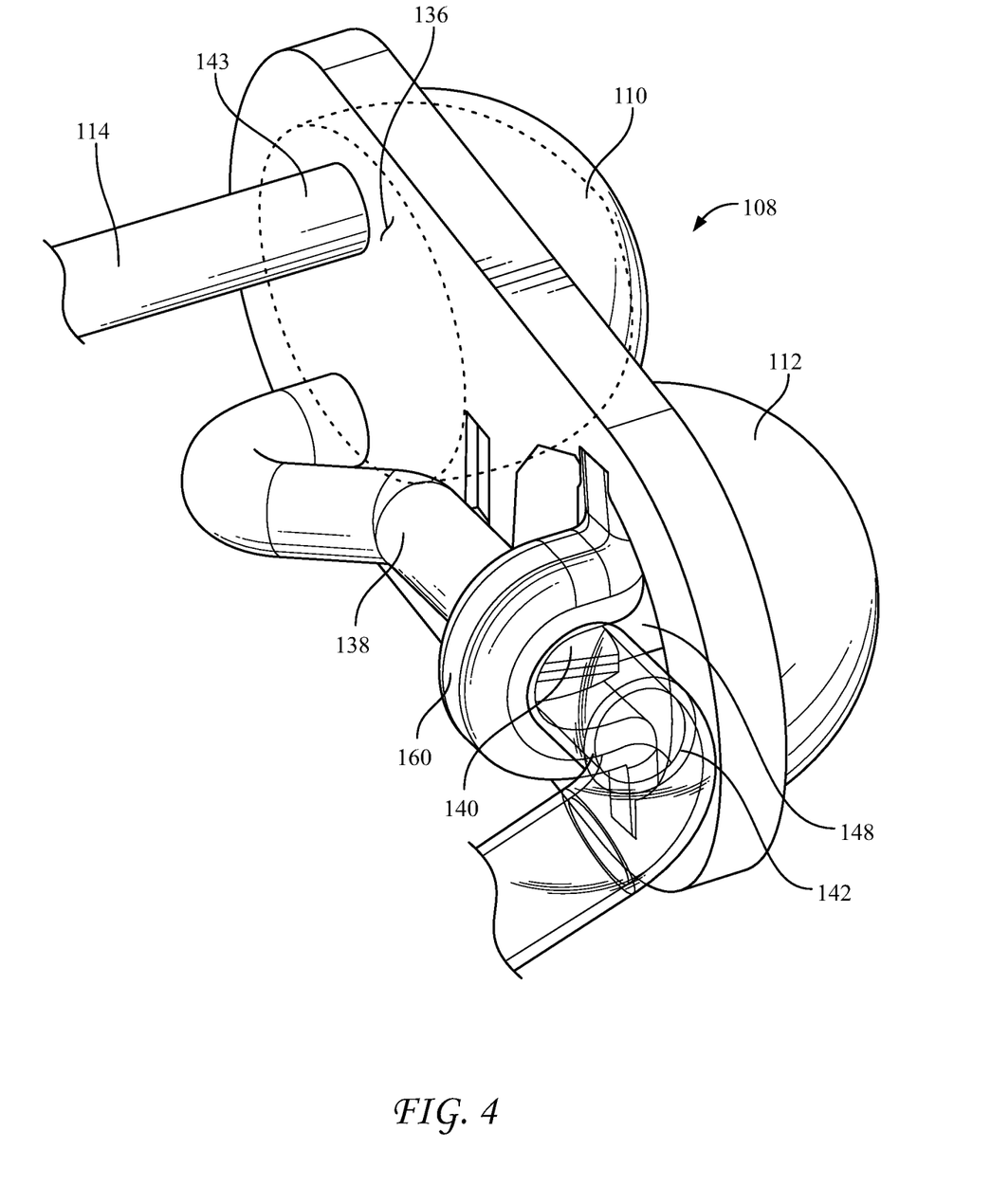

Pump 108 is configured to enable fluid transport between reservoirs 104 and 106. Pump 108 may include a pump chamber 136 and a pump conduit 138. In some embodiments pump conduit 138 is formed integrally with tube 116. In other embodiments, pump conduit is formed separately from but connected to tube 116 (e.g., by a tubing connector, not shown). Implant 100 may further include a first valve 140, which may be included as a component of pump 108 or which may be included separately from pump 108, e.g., between pump 108 and second reservoir 106, i.e., along tube 116. As shown in FIGS. 3 and 4, first valve 140 is disposed proximate pump outlet 142, i.e., a location at or near the location where conduit 138 mates with tube 116. In some embodiments, a second valve (not shown) may be included between first reservoir 104 and pump 108, e.g., within tube 114 or as a component of pump 108 proximate to pump inlet 143, which may facilitate pumping fluid from first reservoir 104 to second reservoir 106 by preventing backflow from pump 108 to first reservoir 104 when pump actuator 110 is depressed.

The valves included within implant 100 should be capable of preventing backflow, i.e., flow from second reservoir 106 to first reservoir 104, such as check valves, duckbill valves, umbrella valves, or X-fragm valves manufactured by Minivalve, Inc., of Cleveland, Ohio. For example, FIGS. 3 and 4 show first valve 140 as a duckbill valve having valve inlet 144 and valve outlet 146. This first duckbill valve 140 is oriented with outlet 146 further from pump actuator 110 than inlet 144, which prevents backflow from second reservoir 106 to first reservoir 104 when the "bill" of the valve is closed. Put another way, assuming the direction of flow is from first reservoir 104 to second reservoir 106, first duckbill valve 140 is downstream from pump actuator 110 and valve outlet 146 is downstream from valve inlet 144. In those embodiments having a duckbill valve as a second valve to help prevent backflow from pump 108 to first reservoir 104, the second duckbill valve should also have a downstream orientation, with the outlet of the second valve closer to pump actuator 110 than the inlet of the second valve. Additional combinations of valves may be used to achieve desired functionalities, as discussed further below.

Pump 108 may further include a release actuator 112, which may include an arm or finger 148. When depressed, release actuator 112 and arm 148 cause first valve 140 to open, thereby allowing backflow. In the embodiment shown, arm 148 may squeeze the bill against a counter feature 160, which deforms the bill, thereby removing the seal maintained by the bill. In such embodiments, other components and features of implant 100 that maintain the position of first valve 140 may also be flexible and deformable, such as tube 116 and/or conduit 138. Those embodiments that include a second valve should also include functionality for opening the second valve. For example, if the second valve is also a duckbill valve, release actuator 112 may include a second arm capable of opening the valve, e.g., by deforming the second valve's "bill" outlet. If the second valve is a check valve, e.g., B. Braun part no. S5401020SN, a second release actuator may be included within implant 100, possibly on pump 108 or elsewhere on shell 102, that may manipulate the check valve into an open position.

In other embodiments a third tube or conduit (not shown) may bypass pump actuator 110 and/or pump 108. The third tube may extend from second reservoir 106 to first reservoir 104, it may fork off of second tube 116 and fork to first tube 114, or some combination thereof. The third tube may also include a backflow prevention valve to prevent backflow from second reservoir 106 to first reservoir 104 when the valve is closed but to permit such backflow when the valve is opened. In some embodiments, release actuator 112 may be configured to open this valve. In other embodiments, another release actuator may be incorporated into implant 100, perhaps on pump 108 or elsewhere on shell 102, to open the valve.

In some embodiments, pump 108 may be disposed entirely within shell 102 as shown in the figures. Alternatively, pump 108 may be partially disposed on the surface of shell 102, about membrane 126. That is, a surface 150 of pump 108 that includes pump actuator 110 and, in some embodiments, release actuator 112, may be disposed on the outer surface of shell membrane 126 whereas the remainder of pump 108 may be disposed on the inner surface of shell membrane 126. Tabs 152 and 154 may be incorporated onto surface 150 to help secure pump 108 to shell 102 if disposed entirely therein or to membrane 126 if disposed partially within shell 102. In those embodiments in which the entirety of pump 108 is disposed entirely within shell 102 pump actuator 110 and release actuator 112 are disposed proximate membrane 126 such that the actuators may be depressed by pressing a portion of membrane 126 near to the actuators. For example, pressing membrane 126 near to actuator 110 depresses actuator 110 and pressing a portion of membrane 126 near to actuator 112 depresses actuator 112.

Tabs 152 and 154 assist in maintaining the position of pump 108 relative to other components of implant 100 by resisting forces applied to pump 108, particularly forces applied to pump actuator 110 and release actuator 112. In some embodiments not shown, pump 108 may be positioned near to the bottom of the shell. As shown in the figures, surface 150 is substantially parallel to the portion of shell membrane 126 closest thereto. In some embodiments, not shown, surface 150 may be angled away from the bottom of the shell relative to the position shown in the figures. This angle may be between approximately 10 degrees and 80 degrees, it may be between approximately 30 degrees and approximately 60 degrees, it may be approximately 45 degrees, or it may be some other range of angles between 10 degrees and 80 degrees. So positioned and oriented, anatomy of a subject may provide further resistance to forces applied to pump 108. For example, where implant 100 is a breast implant, bones in the chest may resist displacement of pump 108, thereby facilitating a subject's ability to manipulate pump actuator 110 and release actuator 112.

In some embodiments, pump actuator 110 and release actuator 112 include resilient elastomeric, e.g., silicone rubber, buttons. An inner surface of pump actuator 110 may comprise an inner flexible surface or wall portion of chamber 136. Accordingly, when pump actuator 110 is depressed, the volume of chamber 136 is reduced from its original volume. When pump actuator 110 is released, the volume of chamber 136 increases back to the original volume. Thus, a portion of the fluid within chamber 136 is expelled from the chamber when pump actuator 110 is depressed and that portion is replaced when pump actuator 110 is released. First valve 140, perhaps in combination with the second valve if the second valve is included, operate in conjunction with actuator 110 to ensure fluid flows in a desired direction, i.e., from first reservoir 104 to second reservoir 106. That is, when actuator 110 is depressed, a volume of fluid is advanced downstream, past first valve 140. When actuator 110 is released, this volume of fluid cannot move backward past valve 140. Accordingly, another volume of fluid is withdrawn from upstream of pump 108. In those embodiments that include the second valve, fluid contained in chamber 136 is further restricted from flowing backward toward first reservoir 104 when actuator 110 is depressed.

Figure 5A:
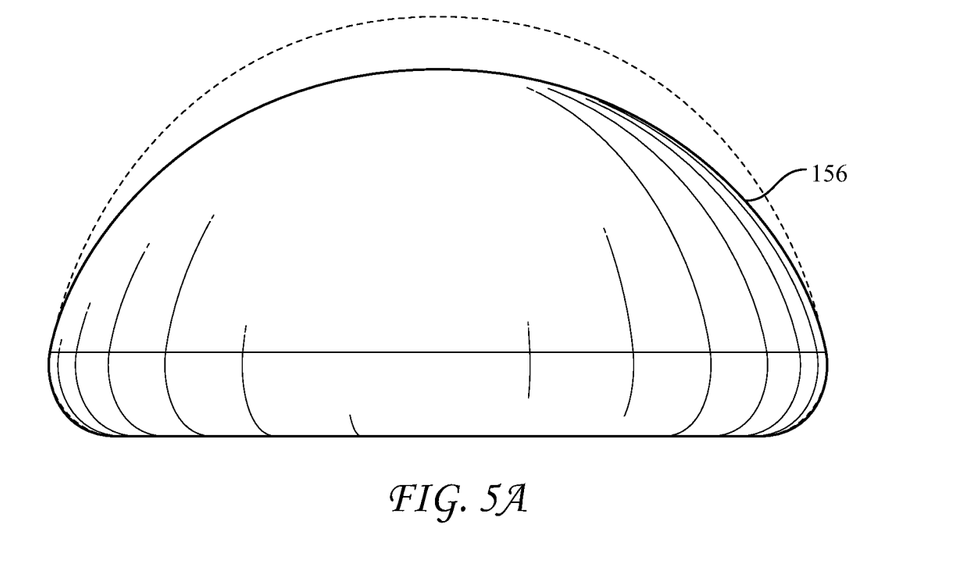
FIGS. 5A and 5B depict the adjustable implant of FIG. 1 in a rest state and an expanded state.
Figure 5B:
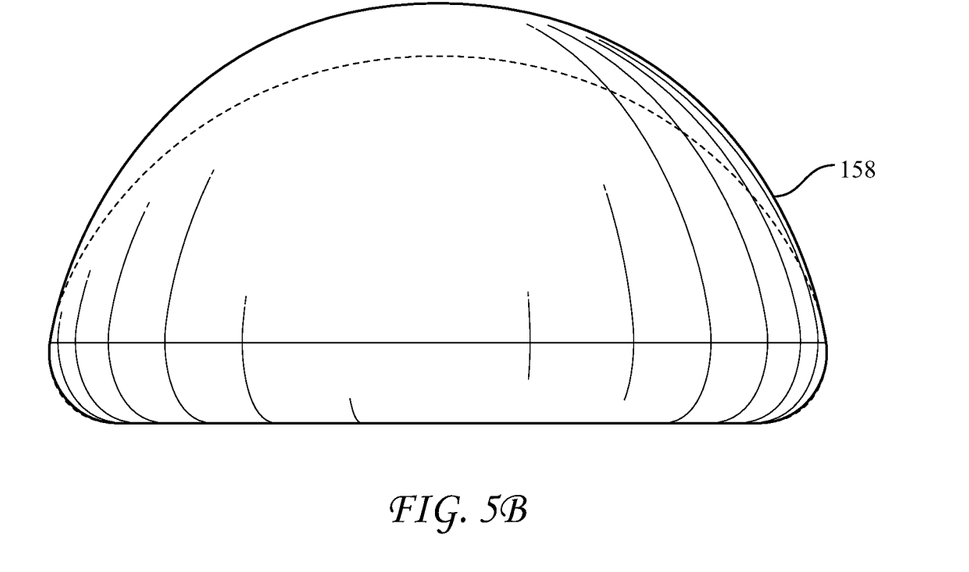

FIGS. 5A and 5B reflect a "before and after" representation of adjustable implant 100. Implant 100 may be expanded from an original volume or rest state 156 (solid lines) to an enlarged volume or expanded state 158 (dotted lines). This change in volume is effected by enlarging the volume of second reservoir 106 by pumping fluid into it from first reservoir 104. The expansion of second reservoir 106 causes second-reservoir membrane 132 to push against material 128 of shell 102, which transfers forces against the inside of shell membrane 126, causing it to expand. In turn, any substance, such as a subject's tissue, against the surface of shell membrane 126, should be displaced.

Implant 100 may thus be utilized according to the following method. Implant 100 may be provided and implanted within a region of a subject's anatomy, such as behind a chest muscle, into an existing breast capsule or pocket that may have been formed with the assistance of a tissue expander. As provided, second reservoir 106 is empty of fluid. The subject or another individual, such as a medical professional, may depress pump actuator 110 by pressing on a portion of the subject's tissue that overlies pump actuator 110. Depressing pump actuator 110 reduces the volume of chamber 136, which forces a first volume of fluid out of the cavity, past first-valve 140 toward second reservoir 106. The first volume of fluid displaces a second volume of fluid already in tube 116 through port 122 into second reservoir 106, which increases the volume of fluid in second reservoir 106. This causes second reservoir 106 to expand by stretching and/or unfolding of pleats 134. Second-reservoir membrane thus pushes against material 128, forcing it outward. In turn, this mechanism causes shell membrane 126 to expand and push against the subject's tissue.

As pump actuator 110 is released, chamber 136 returns to its original volume. This action pulls a third volume of fluid into chamber 136 from tube 114, which in turn removes a fourth volume of fluid from first reservoir 104. However, because reservoir 104 includes enclosure 130, which is made from a rigid or semi-rigid material, enclosure 130 maintains its shape and does not contract in response to fluid being withdrawn from reservoir 104. Furthermore, enclosure 130 is capable of resisting forces generated within material 128 that press against enclosure 130. Accordingly, the expansion of shell 102 caused by the expansion of second reservoir 106 is not lost by a subsequent contraction of reservoir 104 and/or enclosure 130. Therefore, repeatedly depressing and releasing pump actuator 110 causes shell 102 to repeatedly expand in increments corresponding to the amount of fluid each depression expands second reservoir 106. FIGS. 6 and 7 show implant 100 in an expanded configuration, with shell 102 and second reservoir 106 also in expanded configurations. Further, reservoir 104 is shown in FIG. 7 in a collapsed configuration because base 162 has been drawn up, away from its resting position (FIG. 2) by the withdrawal of fluid from within reservoir 104.

The volume of implant 100 may be decreased, potentially to its original size and the volume of shell membrane 126 decreased, also potentially to its original size, by transporting fluid in reverse, from second reservoir 106 to first reservoir 104. Because second reservoir 106, including membrane 132, may be fabricated from an elastomeric material, the expanded state may also be considered a pressurized state. Specifically, membrane 132 may be fabricated from a silicone rubber material having a wall thickness between approximately 0.01 inches and approximately 0.1 inches with a shore A durometer of between approximately 10 and approximately 100. In certain embodiments membrane 132 may have a wall thickness of approximately 0.05 inches with a shore A durometer of approximately 55. Accordingly, when any valves preventing backflow, e.g., first valve 140, are opened, fluid within second reservoir 106 flows toward first reservoir 104. Further, in those embodiments where first reservoir 104 is fabricated from a rigid or semi-rigid material, back-pressure may have been generated by the action of pumping fluid from first reservoir 104 to second reservoir 106. This back-pressure may further assist fluid flow from second reservoir 106 to first reservoir 104 when the valves preventing backflow are opened. Thus, contraction of implant 100 may be performed in steps by repeatedly depressing actuator 112 for short time intervals. Alternatively, implant 100 may be returned to its original volume by holding down actuator 112 for a sufficiently long time interval.

In use, a subject may adjust the projection of implant 100 in increments by using pump 108 to convey fluid between reservoirs 104 and 106. Accordingly, a subject may adjust, or fine tune, the projection of implant 100 without the assistance of a healthcare provider, such as a breast-reconstruction surgeon, and without adding or removing any fluid from implant 100, steps that are required in the case of tissue expanders or conventional adjustable implants, such as Mentor's Becker Expander/Mammary Prostheses. The subject may perform these adjustments privately, with ease, and whenever desired.

Figure 8:
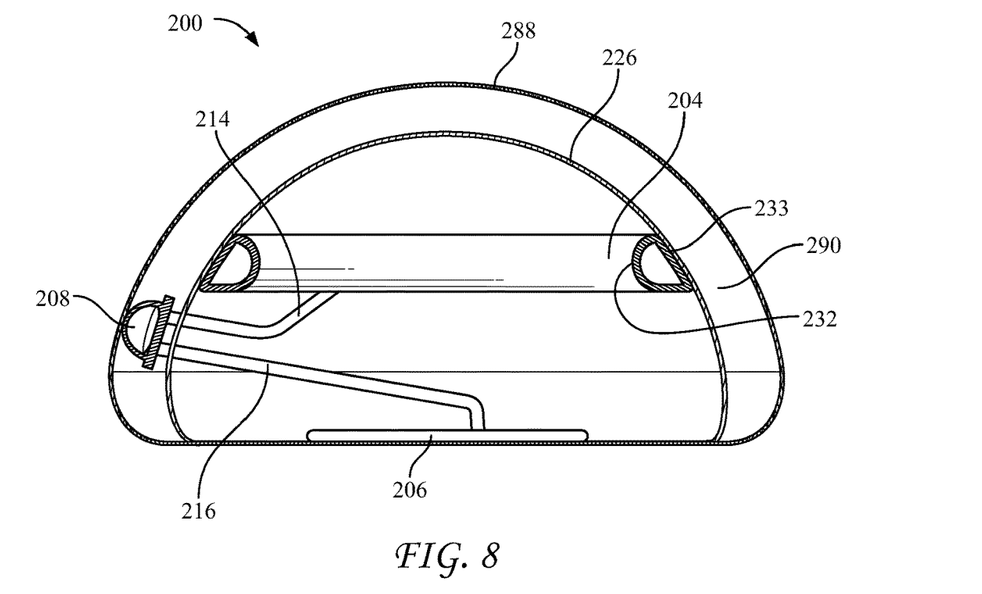
FIG. 8 depicts an alternate embodiment of an adjustable implant in an unexpanded state.
Figure 9:
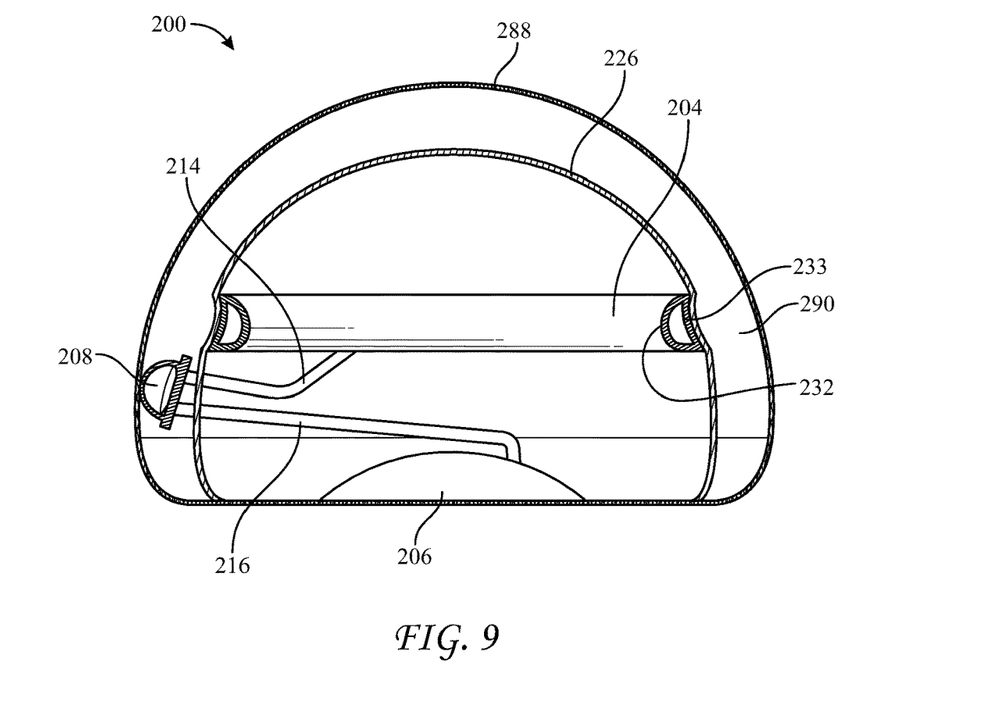
FIG. 9 depicts the adjustable implant of FIG. 8 in an expanded state.

FIGS. 8 and 9 reflect alternative embodiments of an adjustable implant concerning the first reservoir. As shown, implant 200 includes a first reservoir 204, which has a toroidal configuration, and a second reservoir 206. As shown in FIGS. 8 and 9, first reservoir 204 and second reservoir 206 may be affixed to portions of membrane 226. However, in some embodiments, they need not be affixed thereto. For example, first reservoir 204 may be suspended within implant 200, which may be itself be a body of a material, such as silicone rubber or silicone gel. Alternatively, first reservoir 204 may be disposed proximate an inferior portion of implant 200, i.e., proximate the bottom of implant 200, to assist in minimizing detectability of curvature changes in membrane 226, explained below, through a subject's skin. Similarly, second reservoir 206 may be positioned at locations within implant 200 other than those reflected in the figures.

The two reservoirs 204 and 206 are in fluid communication via tubing 214, pump 208, and tubing 216. In some embodiments, first reservoir 204 may comprise a first membrane 232 and a second membrane 233. However, in some embodiments, first membrane 232 and second membrane 233 may be fabricated as a single component or from multiple components that are bonded to each other, e.g., by ultrasonic welding or silicone glue. An advantage of using two or more membranes is that the physical properties, such as hardness and elasticity, of each membrane may be chosen to achieve desired functionality of first reservoir 204. In some embodiments, first membrane 232 and second membrane 233 may have the same hardness, whereas in other embodiments they may have different hardnesses. Accordingly, e.g., both membranes may be rigid, both may be flexible, one may be rigid while the other is flexible, or some other combination.

In some embodiments, first membrane 232 and/or second membrane 233 may be rigid or semi-rigid such that they may maintain their shape irrespective of whether fluid is disposed therein. In those embodiments where at least a portion of first reservoir 204 and/or second reservoir 206 is not entirely rigid, fluid may be used to expand and contract the non-rigid portions of the reservoir(s), e.g., membrane 232 and/or 233.

When fluid is absent from either reservoir, that reservoir is empty and in a contracted or partially contracted configuration. However, when fluid is disposed within either reservoir, that reservoir is in an expanded or stretched configuration. As shown in FIG. 8, first reservoir 204 has an expanded configuration and second reservoir 206 has a contracted configuration. As shown in FIG. 9, first reservoir 204 is in a partially contracted configuration and second reservoir 206 is in a partially expanded configuration.

In some embodiments first membrane 232 is rigid or semi-rigid and second reservoir 233 is flexible. In these embodiments, when first reservoir 204 is full (FIG. 8), the portion of shell membrane 226 to which second membrane 233 is affixed has a concave profile (relative to the interior of reservoir 204) having a curvature that is substantially similar to the curvature of neighboring portions of shell membrane 226. However, when first reservoir is partially or entirely empty (FIG. 9), the curvature of the portion of shell membrane 226 to which second membrane 233 is affixed changes. That is, it inverts to become convex (relative to the interior of reservoir 204). As fluid is pumped out of reservoir 204, second membrane 233 is displaced toward rigid or semi-rigid first membrane 232. This displacement pulls shell membrane 226 inward, thereby creating the convex portion of shell membrane 226. Thus, the profile of the portion of shell membrane 226 that is affixed to the second membrane 233 depends on the amount of fluid within reservoir 204.

In those embodiments where first membrane 232 is semi-rigid or flexible and second membrane 233 is rigid, the profile of first membrane 232 may more closely approximate the profile of second membrane 233 when first reservoir 204 is empty or partially empty (not shown) than when first reservoir 204 is full (FIG. 8). Thus, the profile of the portion of shell membrane 226 that is affixed to the second membrane 233 depends minimally on the amount of fluid within reservoir 204.

The height of implant 200 is greatest when reservoir 206 is full (FIG. 9) and least when reservoir 206 is empty (FIG. 8). Accordingly, in those embodiments where second membrane 233 is rigid, the contour of shell membrane 226 may be maintained substantially constant, including along the portion that is affixed to second membrane 233, irrespective of the amounts of fluid in contained in the reservoirs. Thus, the expansion of shell membrane 226 caused by an increase in volume to second reservoir 206 may be focused into making shell membrane 226 grow taller instead of wider. However, the rigidity of second membrane 233 may inhibit removal of fluid therefrom. In those embodiments where second membrane 233 is flexible, the contour of shell membrane 226 may be changed to convex while allowing fluid to be readily withdrawn from first reservoir 204.

Because such a change in curvature may be undesirable to a subject, implant 200 may optionally be disposed within a volume of material, such as a silicone gel 290, enclosed within a second shell membrane 288. Such embodiments may be referred to as a being "double implant" embodiments. In these embodiments membrane 288 maintains a substantially uniform curvature irrespective of the local displacement of membrane 226 from second membrane 233.

Figure 10:
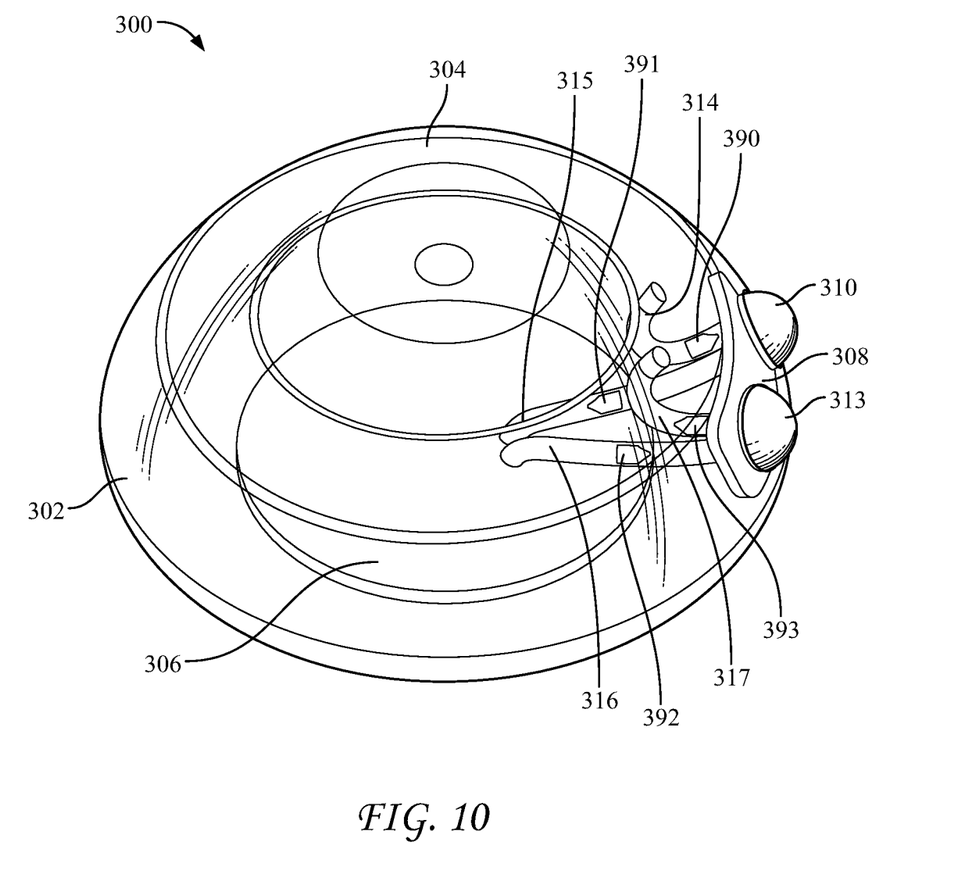
FIG. 10 depicts an alternate embodiment of an adjustable implant.
Figure 11:
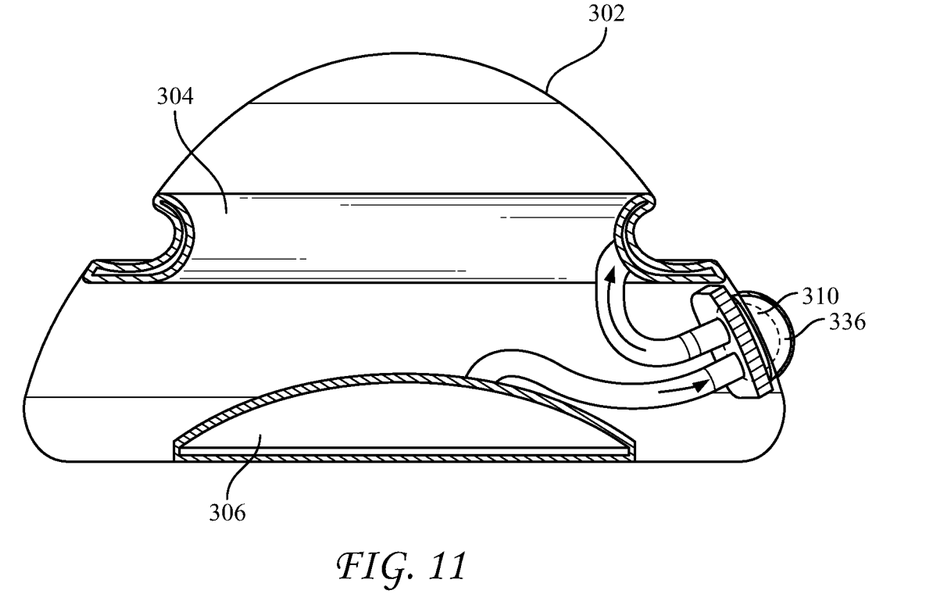
FIG. 11 depicts a cross section of the embodiment of FIG. 10 in an expanded state.

FIGS. 10 and 11 show implant 300. Implant 300 includes a toroidal first reservoir 304, similar to the toroidal first reservoir 204 described above. Implant 300 includes a pump apparatus 308 that has a first pump actuator 310 and a second pump actuator 313. As shown, this embodiment does not include a release actuator, although one may be included if the corresponding functionality, described above, is desired. First reservoir 304 and second reservoir 306 are fluidly connected via two distinct fluid paths. The first path comprises tube 314, first pump actuator 310, and tube 315. The second path comprises tube 316, second pump actuator 313, and tube 317. First pump actuator 310 may be used to advance fluid toward second reservoir 306 and second pump actuator 313 may be used to advance fluid toward first reservoir 304. As with the embodiments described above, the profile of shell 302 may be changed, e.g., made taller, by pumping fluid from first reservoir 304 into second reservoir 306 to expand second reservoir 306. Depressing first pump actuator 310 advances fluid contained within a first chamber of pump actuator (not shown, refer to chamber 136 and second chamber 336) toward second reservoir 306 along tube 315 and releasing first pump actuator 310 draws fluid into the first chamber from tube 314. Depressing second pump actuator 313 advances fluid contained within second chamber 336 toward first reservoir 304 along tube 317 and releasing second pump actuator 313 draws fluid into second chamber 336 from tube 316. Thus, by pressing and releasing first pump actuator 310, first reservoir 304 may be contracted and second reservoir 306 may be expanded. Conversely, by pressing and releasing second pump actuator 313, second reservoir 306 may be contracted and first reservoir 304 may be expanded. Accordingly, pump actuator 310 may be repeatedly pressed to transfer substantially all of the fluid within reservoir 304 out of reservoir 304 and into reservoir 306. In FIG. 10, shell 302 has a "short" profile because first reservoir 304 is substantially full and second reservoir 306 is substantially empty. In FIG. 11, shell 302 has a "tall" profile because first reservoir 304 is substantially empty and second reservoir 306 is substantially full. However, fine tuning of the profile of shell 302 may also be accomplished to achieve a desired profile somewhere between the short and tall profiles reflected in FIGS. 10 and 11. For example, a subject may desire to expand shell 302 to be a particular profile that is taller than the short profile but shorter than the tall profile. To achieve this, and assuming reservoir 304 is full, she may repeatedly depress first pump actuator 310 to pump fluid to second reservoir 306 until she achieves that size. The profile of shell 302 may also be adjusted in small increments in either flow direction. For example, if the subject over expands shell 302, she may contract it with depressions of second pump actuator 313

Valves may be provided in various configurations and combinations within the implant. Using implant 300 as an example, valves may be incorporated into the design such that only single directional flow is permitted along each of the two distinct fluid paths. For example, flow may be permitted along the first path (i.e., tube 314, first pump actuator 310, and tube 315) only in a direction towards second reservoir 306 from first reservoir 304, whereas flow may be permitted along the second path (tube 316, second pump actuator 313, and tube 317) only in a direction towards first reservoir 304 from reservoir 306. This flow pattern may be achieved by positioning valves within some or all of tubes 314, 315, 316, and 317. For example, duckbill valve 390 may be positioned in tube 314 pointing toward first pump actuator 310, duckbill valve 391 may be positioned in tube 315 pointing toward second reservoir 306, duckbill valve 392 may positioned in tube 316 pointing toward second pump actuator 313, and duckbill valve 393 may be positioned in tube 317 pointing toward first reservoir 304. Additional valves (e.g. from Mini-Valve corporation), such as X-fragm valves or umbrella valves may be included at the inlet of one or more of the duckbill valves 390-393 to open only when first pump actuator 310 or second pump actuator 313 are depressed, thereby ensuring that flow only occurs when intentional depressing of the pump actuators occur.

Figure 12:
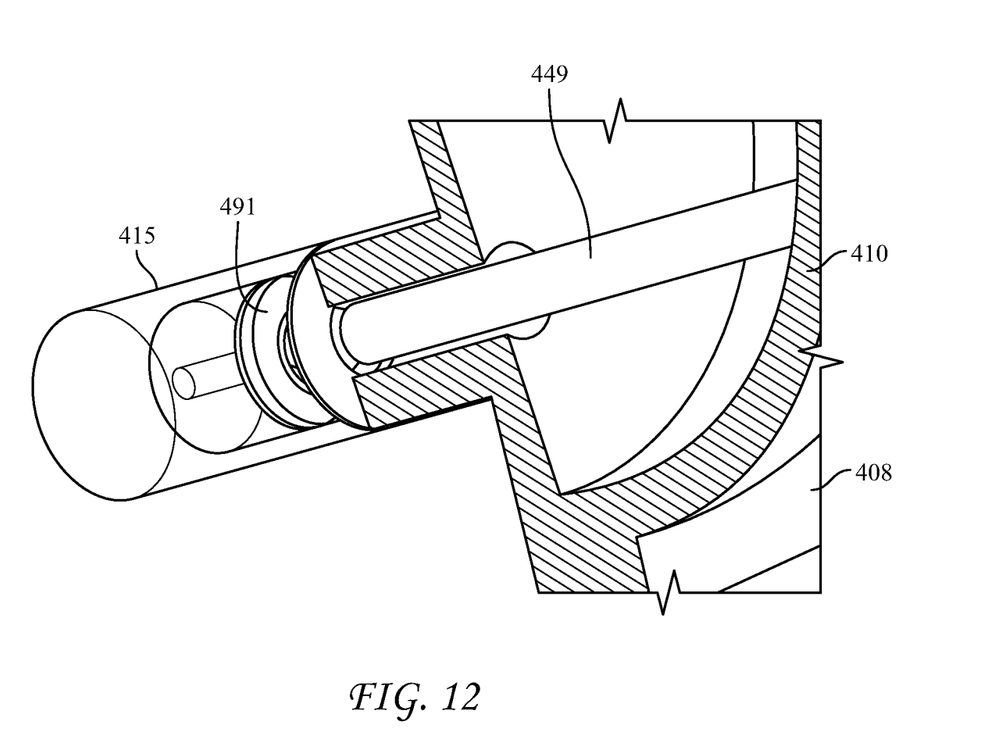
FIG. 12 depicts a section view of a pump actuator.

In some embodiments, one or more of duckbill valves 390-393 may be removed or replaced with another type of valve, such as an open-close valve or a check valve. Ideally, these valves are designed to be in a closed configuration such that they prevent flow until they are mechanically opened. FIG. 12 reflects a magnified section view of pump 408 about first pump actuator 410 and its outlet into tube 415. Within tube 415 is open-close valve or check valve 491 (e.g., B. Braun Part No. S5401033SN; Qosina Part Nos. 80063 or 80466). A finger or arm 449 may be included as part of first pump actuator 410 that may be displaced to open valve 491 such that fluid may be advance past it when pump actuator 410 is depressed. Valve 491 returns to its closed configuration when pump actuator 410 is released because arm 449 returns to its original position.

It should be understood that any of the examples and/or embodiments described herein may include various other features in addition to or in lieu of those described above. The teachings, expressions, embodiments, examples, etc. described herein should not be viewed in isolation relative to each other. Various suitable ways in which the teachings herein may be combined should be readily apparent to those of ordinary skill in the art in view of the teachings herein.

Having shown and described exemplary embodiments of the subject matter contained herein, further adaptations of the methods and systems described herein may be accomplished by appropriate modifications without departing from the scope of the claims. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. A method of using an adjustable implant, comprising: providing the adjustable implant, the adjustable implant having
   a shell including a resilient shell membrane,
   a first reservoir disposed within the shell and containing a first volume of a fluid;
   a second reservoir including a resilient elastomeric second-reservoir membrane disposed within the shell,
   a pump having
      a pump outlet,
      a pump actuator comprising an elastomeric button, the elastomeric button defining a chamber, the chamber containing a second volume of the fluid, and
      a first valve disposed proximate the pump outlet,
   wherein the first reservoir and second reservoir are in fluid communication via the pump and first valve;
   depressing the elastomeric button;
   advancing at least a portion of the second volume of the fluid past the first valve;
   releasing the elastomeric button; and
   withdrawing a third volume of the fluid from the first reservoir.

2. The method of claim 1, further comprising:
   introducing a fourth volume of the fluid into the second reservoir;
   expanding the resilient elastomeric second-reservoir membrane to account for the fourth volume of the fluid entering the second reservoir; and
   expanding the resilient shell membrane in response to expanding the resilient elastomeric second-reservoir membrane.

3. The method of claim 2, wherein the pump further includes a release actuator disposed proximate the first valve and configured to open the first valve when actuated, the method further comprising:
   actuating the release actuator;
   opening the first valve to allow a fifth volume of the fluid to exit the second reservoir and flow toward the first reservoir;
   contracting the resilient elastomeric second-reservoir membrane to account for the fifth volume of fluid exiting the second reservoir; and
   contracting the resilient shell membrane in response to contracting the resilient elastomeric second-reservoir membrane.

4. The method of claim 3, wherein the pump further has a pump inlet, the adjustable implant further has a second valve disposed proximate the pump inlet, and the release actuator is disposed proximate the second valve and configured to open the second valve when actuated, the method further comprising opening the second valve using the release actuator.

5. The method of claim 4, wherein the adjustable implant is a breast implant and further comprising implanting the adjustable implant in a subject.

6. The method of claim 4, wherein the adjustable implant includes a a first tube connected to the first reservoir and the pump inlet, and a second tube connected to the pump outlet and the second reservoir.

7. The method of claim 4, in which the first valve comprises a backflow prevention valve having a first-valve outlet disposed further from the first pump actuator than a first-valve inlet.

* * * * *